(12) United States Patent
Wan

(10) Patent No.: US 7,612,891 B2
(45) Date of Patent: Nov. 3, 2009

(54) MEASUREMENT OF THIN FILMS USING FOURIER AMPLITUDE

(75) Inventor: Der-Shen Wan, Tucson, AZ (US)

(73) Assignee: Veeco Instruments, Inc., Tucson, AZ (US)

( * ) Notice: Subject to any disclaimer, the term of this patent is extended or adjusted under 35 U.S.C. 154(b) by 355 days.

(21) Appl. No.: 11/300,945

(22) Filed: Dec. 15, 2005

(65) Prior Publication Data

US 2007/0139656 A1 Jun. 21, 2007

(51) Int. Cl.
*G01B 11/02* (2006.01)
(52) U.S. Cl. ...................................... 356/503
(58) Field of Classification Search ................. 356/503, 356/504, 479, 497, 630–632
See application file for complete search history.

(56) References Cited

U.S. PATENT DOCUMENTS

| | | | |
|---|---|---|---|
| 6,545,763 B1 * | 4/2003 | Kim et al. | 356/503 |
| 6,624,894 B2 | 9/2003 | Olszak et al. | |
| 7,106,454 B2 * | 9/2006 | De Groot et al. | 356/511 |
| 2002/0196450 A1 * | 12/2002 | Olszak et al. | 356/511 |
| 2006/0176522 A1 * | 8/2006 | Mansfield et al. | 358/474 |

* cited by examiner

*Primary Examiner*—Tarifur Chowdhury
*Assistant Examiner*—Jonathan M Hansen
(74) *Attorney, Agent, or Firm*—Antonio R. Durando

(57) ABSTRACT

Thin-film thickness and refractive index are measured using the Fourier amplitude of a broadband interferometric spectrum. Due to the smooth nature of the Fourier amplitude as a function of wavelength, as compared to the fast varying Fourier phase conventionally used to measure thickness, increased stability and repeatability of measurement are achieved. As a result, measurements of ultra-thin films with thickness below 100 nm are possible with reliable results.

22 Claims, 8 Drawing Sheets

MEASUREMENT OF THIN FILMS USING FOURIER AMPLITUDE

BACKGROUND OF THE INVENTION

1. Field of the Invention

This invention relates in general to techniques for measuring the characteristics of thin films. In particular, it relates to white-light scanning interferometric methods and systems for measuring the thickness of transparent thin-film coatings.

2. Description of the Related Art

White-light scanning interferometers (WLSIs) have gained popularity in opto-electronic industry for testing that goes beyond measuring the thickness of various elements of opto-electronic circuitry. The measurement technique of white-light scanning interferometry produces a short coherence interferogram that enables the measurement of the optical path difference between test and reference beams without $2\pi$ ambiguity. Unlike other conventional techniques, such as ellipsometry or spectroscopy, which cannot measure surface profile, this interferometric technique can produce both thickness and surface profile measurements of a transparent object under test, thus effectively providing the user with information about its three-dimensional profile.

As is well understood in the art, a WLSI utilizes interferometric signals (often referred to as correlograms) generated by changing the length of the sample arm of the interferometer with respect to its reference arm in minute incremental steps (typically, several nanometers long) within the coherence length of the light utilized for the measurement. The interferometric signal produced by an uncoated substrate (whether flat or patterned) clearly differs from the signal produced by a substrate coated with a thin film because of the multiple reflections generated within the film. Accordingly, these two signals can be used to determine the thin-film thickness distribution. U.S. Pat. No. 6,545,763 by Kim et al. describes a method for extracting thin-film thickness and profile data from the Fourier transform of the interferometric correlogram produced by a substrate coated with a thin film. The approach makes use of the dependency of the phase component of the Fourier transform on film thickness. The spectral phase information is compared to the phase information obtained by modeling the measurement and an error function is generated and minimized. This approach has shown not to provide repeatable results when the thickness of the film is reduced to about a tenth of a micron or below.

Since the fabrication of dielectric coatings with sub-micron thickness (i.e., below the white-light coherence length of about several microns) is quite common and becomes even more demanding with advances in short-wavelength optical technologies, there remains a need for developing a technique for measuring accurately and repeatably the parameters of dielectric films with a thickness on the order of 100 nm or less. This problem is solved in the present invention by utilizing the amplitude components of the Fourier transform ("Fourier amplitude") of WLSI correlograms. The approach also produces information about the three-dimensional (volumetric) profile of the thin film and may be extended to provide information about the film's index of refraction.

BRIEF SUMMARY OF THE INVENTION

The invention consists of utilizing the amplitude component of the Fourier transform of the white-light interferogram obtained during the measurement of a thin-film-coated surface to extract information about the thickness of the film. In its basic embodiment, the procedure involves a simple sequence of experimental and computational steps.

First, a reference measurement is made to obtain a reference correlogram using a substrate of known and preferably constant reflectivity over the measurement spectrum. The Fourier amplitude corresponding to the correlogram is used to calculate a table of reference values, as a function of wavelength, for the light-source and the reference-beam amplitude contributions to the correlogram's Fourier amplitude. A test measurement is then made with the substrate and film of interest and the corresponding test correlogram is recorded. The Fourier amplitude corresponding to the test correlogram and the reference values of the Fourier amplitude contribution from the light source and the reference beam are used to derive the experimental Fourier amplitude contribution of the test beam, which is known to be a function of wavelength as well as film thickness.

This experimentally derived Fourier amplitude contribution of the test beam is then compared to its theoretical value, as defined by a theoretical equation for the thin-film reflection coefficient of a system with multiple-beam fringes in a plane-parallel plate. This comparison is preferably expressed as an error function that is then minimized as a function of film thickness. The thickness corresponding to the minimum value of the error function is taken as the film thickness produced by the measurement. In practice, the experimental test-beam amplitude is judiciously matched with the appropriate spectral amplitude obtained, as a function of film thickness, from the theoretical equation modeling the reflection of the thin film. The best match produces the thickness of the thin film at the point of reflection on the sample surface. As those experienced in interferometric measurements readily understand, the multi-pixel data produced by a vertical scan would produce corresponding film-film thickness values for the entire area covered by the scan.

As mentioned, a serious problem with the prior-art Fourier-phase approach resides in the fact that, as the thickness of the film is reduced, the phase of the multiple reflections in the film changes extremely quickly and, at some point (at about 0.1 micron or so), the phase to be measured is a small quantity (on the order of 0.01 to 0.02 radians—or 0.003 of a wavelength). Since the Fourier amplitude of a white-light interferogram spectrum (unlike its Fourier phase component) is a smooth function of wavelength, even for ultra-thin films the amplitude produces significantly more repeatable and robust results based on the same experimental procedure. Therefore, this problem is overcome by the Fourier-amplitude approach of the invention, which enables repeatable measurements of thickness of ultra-thin films on the order of about 0.1 micron. In particular, the method of the invention is expected to perform strongly even with extremely thin films (less than 0.1 micron). Additionally, unlike the prior-art approach, the method of the invention does not require initial guesses about the profile of the substrate surface.

According to another aspect of the invention, the procedure also makes it possible to determine the index of refraction of the thin film. Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DETAILED DESCRIPTION OF THE INVENTION

Figure 1:
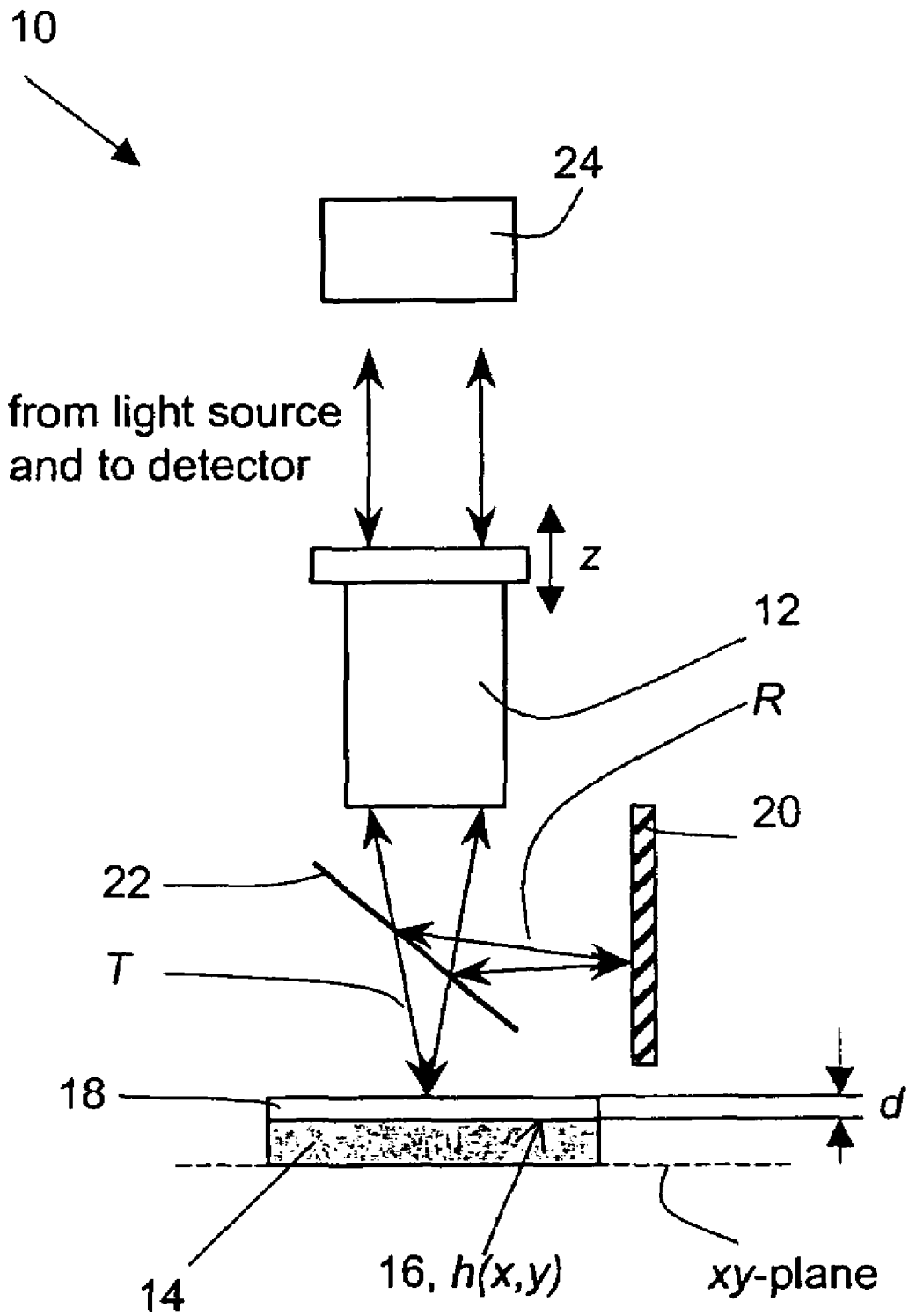
FIG. 1 is a schematic illustration of a conventional white-light scanning interferometer in Michelson configuration.

It is understood that the invention may be practiced with any conventional scanning interferometer, such as a Michelson, Mireau, or Linnik interferometer. The basic schematic configuration of a Michelson scanning interferometer 10 is illustrated for example in FIG. 1. An actuator (not shown) moves the objective 12 of the interferometer along the z axis (typically vertical) with respect to a test substrate 14 located on a stage (not shown) in the xy plane (typically horizontal). Alternatively, the substrate under test may be moved relatively to the objective. The test surface 16 of the substrate 14 has a profile h(x,y) and may be uncoated or coated with a thin film 18 of thickness d. A reference mirror 20 and a beam splitter 22, dividing the incident light received from the light source (not shown) into reference and test beams R and T, respectively, are positioned in front of the objective 12. The resulting white-light interferogram measured by a detector 24 is a low-coherence superposition of individual interferograms of all monochromatic waves that comprise the spectrum of the light source.

The invention is described in terms of white light because it is based on information derived from a spectrum, but it is understood that any broadband light with sufficient bandwidth to produce an interferogram representative of multiple wavelengths is suitable to practice the invention. Accordingly, the term "broadband" light is used herein to refer to any light with at least two wavelengths sufficiently separated to produce spectral information. It is also understood that, inasmuch as the invention is based on the minimization of an error function that contains wavelength as a parameter, a more precise result will be obtained from data produced with a greater number of wavelengths, especially as the film thickness is reduced. Therefore, though not critical, the use of white light is preferred. Furthermore, in the context of the spectral distribution of a light beam, the terms "wavenumber" and "wavelength" are used interchangeably for simplicity, it being understood that one is the reciprocal of the other.

It is also understood that the generic terms "film" and "thin film," used for simplicity throughput the specification of the invention, are intended to refer to any liquid as well solid layers of materials coating a substrate, and to solid plates that may be combined with a substrate without being attached to it. In essence, any layer of material lying over a substrate is considered a film for the purposes of this invention. The same definition is meant to apply with reference to multi-layer structures of different films over a substrate.

The interferometric intensity I(z) sampled in reflection mode by the detector of an interferometer from a point (x,y) on a substrate under test is expressed in the art as a double integral, $$I(z) = \gamma \int_k F(k, d) \int_\theta \cos[2k(h-z)\cos\theta + \phi(k, d, \theta)]\sin\theta\cos\theta\, d\theta\, dk, \quad (1)$$

where γ denotes the modulation amplitude and k is the wavenumber. The outer integral is performed over the spectral bandwidth of the white-light source, while the inner integral is performed over the range of angles θ spanning the full numerical aperture of the objective. The information about the film thickness d, contained in both the spectral amplitude F(k,d) and the spectral phase φ(k,d,θ), can be retrieved using the Fourier transform of the correlogram. The Fourier amplitude F(k,d) results from the product of three terms $$F(k,d) = S(k)a(k)b(k,d), \quad (2)$$

where the function S(k) describes the spectrum of the light source (and incorporates the spectral responsivity of the detector), a(k) is the spectral amplitude of the reference beam, and b(k,d) is the spectral amplitude of the reflected test beam, which contains the information about the film thickness.

Figure 2:
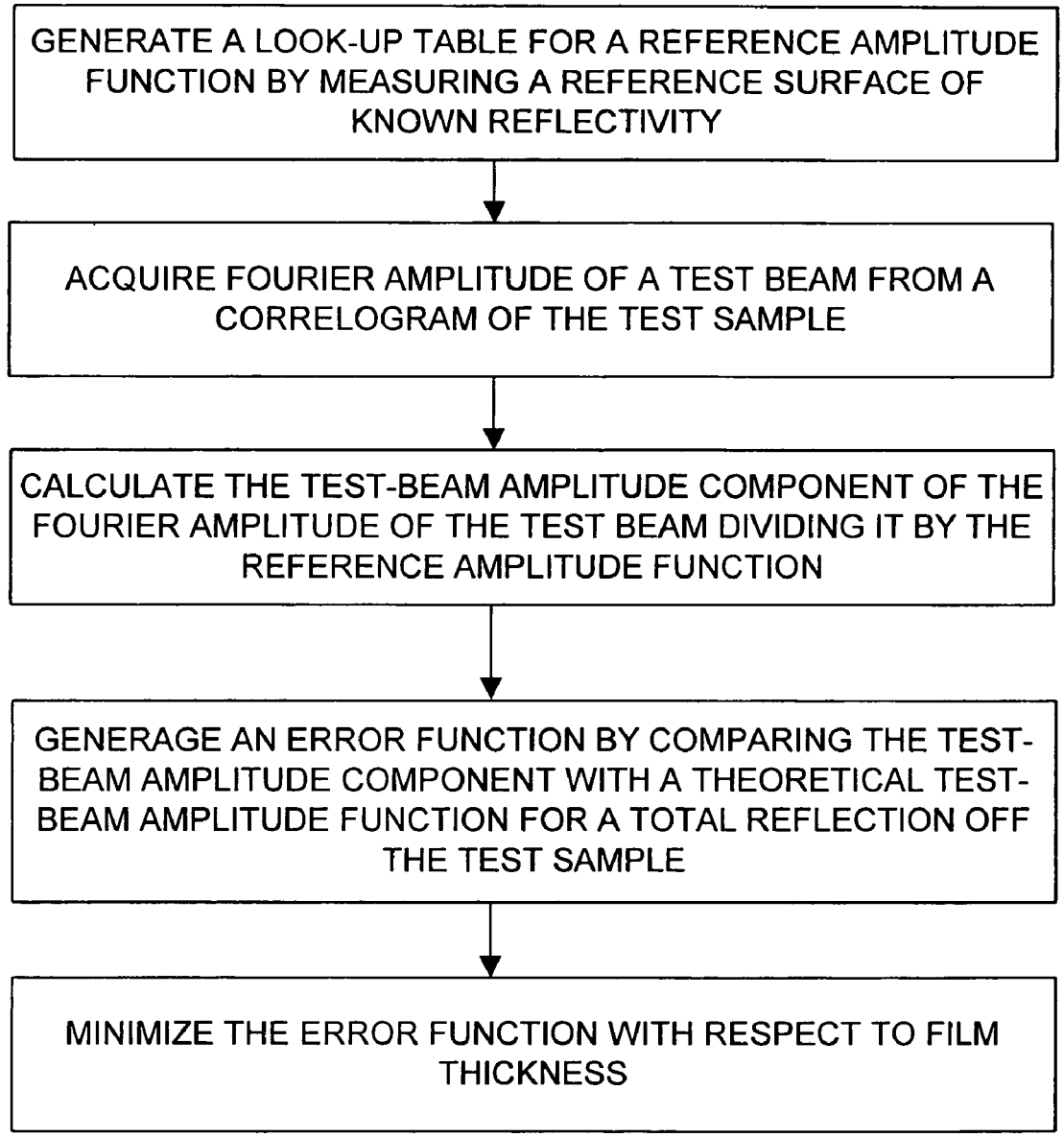
FIG. 2 is a flow-chart showing the steps for measuring the thickness of thin transparent coatings according to the invention.

FIG. 2 is a flow-chart of the method of the invention as applied to measuring the thickness d of a thin film overlaying the surface 16 of a substrate 14. The initial step requires the calibration of the instrument to determine the contributions of the light source and the reference beam to the Fourier amplitude derived from each correlogram produced by the system. The calibration involves an independent measurement of interferometric fringes produced by an uncoated reference surface with a known reflectivity over the spectral range of the light source. In practice, this is achieved by using a material, such as silicon, that has a reflectivity over the white-light spectrum that is well known in the art. Using Equation 2 at each wavelength k yields $F(k)=S(k)a(k)b(k)_{ref}$, from which $S(k)a(k)=F(k)/b(k)_{ref}$, where $b(k)_{ref}$ is the prior known amplitude from the reference substrate. Thus, as a result of such calibration, a look-up table for the "reference" amplitude function S(k)a(k) is obtained (that is, a table of S•a values, the amplitude contribution of the source and reference beams to the reflected beam, as a function of wavelength).

The calibration step is followed by the step of obtaining the spectrum of the interferogram produced by the coated substrate 14 and finding the corresponding test spectral amplitude b(k,d) of the reflected test beam T. This is achieved by producing a test interferogram of the sample of interest, producing a corresponding Fourier transform, and then simply dividing the test Fourier amplitude F(k,d) by the previously stored reference amplitude function, S(k)a(k), as follows from Equation 2 above, $$b(k, d) = \frac{F(k, d)}{S(k)a(k)}. \quad (3)$$

Once the test spectral amplitude b(k,d) of the test beam is so found, it is compared to the theoretical amplitude function b'(k,d) included in a theoretical equation for the coefficient of reflection ρ(k,d) produced by a thin-film layer as a result of multiple-beam interference within the thin film. (See M. Born and E. Wolf, Principles of Optics, 7$^{th}$ Edition, Cambridge University Press, p. 361.) This coefficient accounts for the effects of multiple-beam interference within the layer as a function of the layer's thickness d and the wavenumber k, and is expressed as follows, $$\rho(k, d) = \frac{r_{01} + r_{12}\exp(-i2\delta)}{1 + r_{01}r_{12}\exp(-i2\delta)} \quad (4)$$
$$= b'(k, d)\exp[i\phi(k, d, \theta)],$$

where $r_{01}$ and $r_{12}$ are the Fresnel coefficients of reflection at the incident-medium/thin-film and thin-film/substrate boundaries, respectively, $\delta = 2knd\cos\theta$ is the phase difference between consecutive reflections off the film, n is the refractive index of the film at wavenumber k, and θ is the refractive angle in the film.

Based on Equation 4, a merit or error function may be defined as the difference between the values b and b' as a function of film thickness d. Conventional minimization of the error function with respect to d provides the solution to the film thickness problem with respect to the surface point to which the test correlogram pertains. Repeating the procedure for every pixel of interest on the sample surface, the entire thin-film thickness profile may be derived. It is readily understood that, once the thickness of the film is known across the surface 16 of the substrate 14, this information also provides the basis for calculating the three-dimensional, volumetric profile of the film and, if the profile h(x,y) of the substrate is known, also the surface profile of the thin film.

Figure 3:
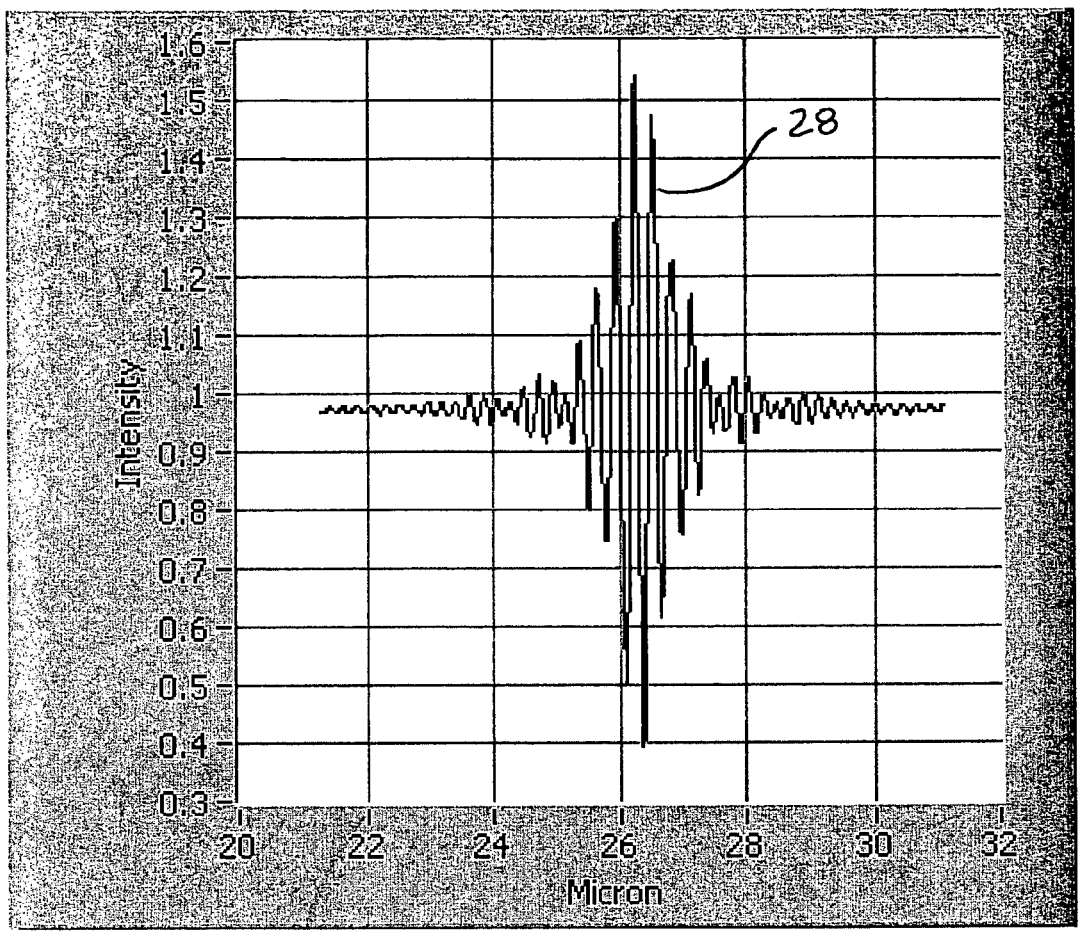
FIG. 3 illustrates a WLSI correlogram produced by a $SiO_2$ film of approximately known thickness (121.5+/−3 nm) over a Si substrate.
Figure 4:
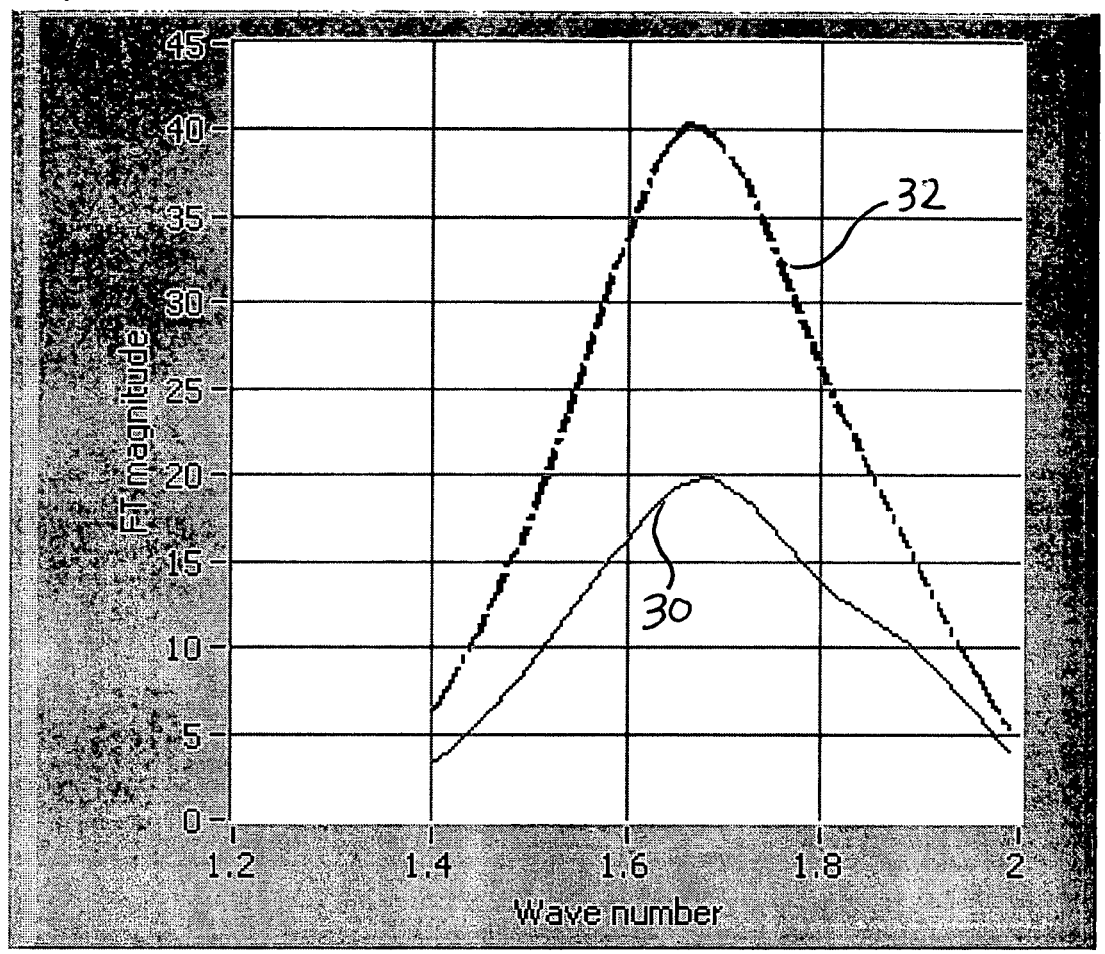
FIG. 4 shows the spectral distribution of the Fourier amplitude derived from the correlogram of FIG. 3 and from the reference substrate.
Figure 5:
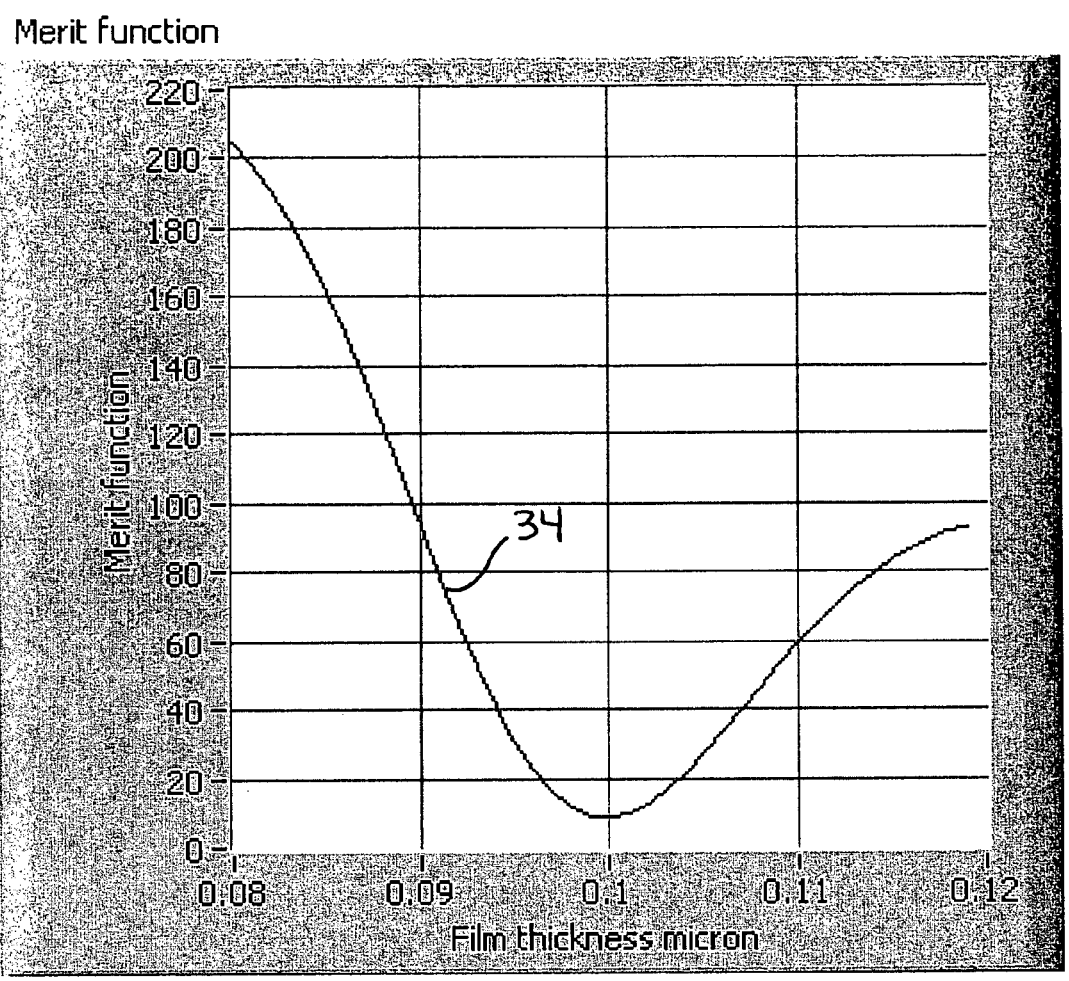
FIG. 5 is a plot of the error function generated by comparing the experimental test beam amplitude calculated from the Fourier amplitude of FIG. 4 with the theoretical value derived from the equation for multiple-beam interference in a film modeled by a plane-parallel plate.
Figure 6:
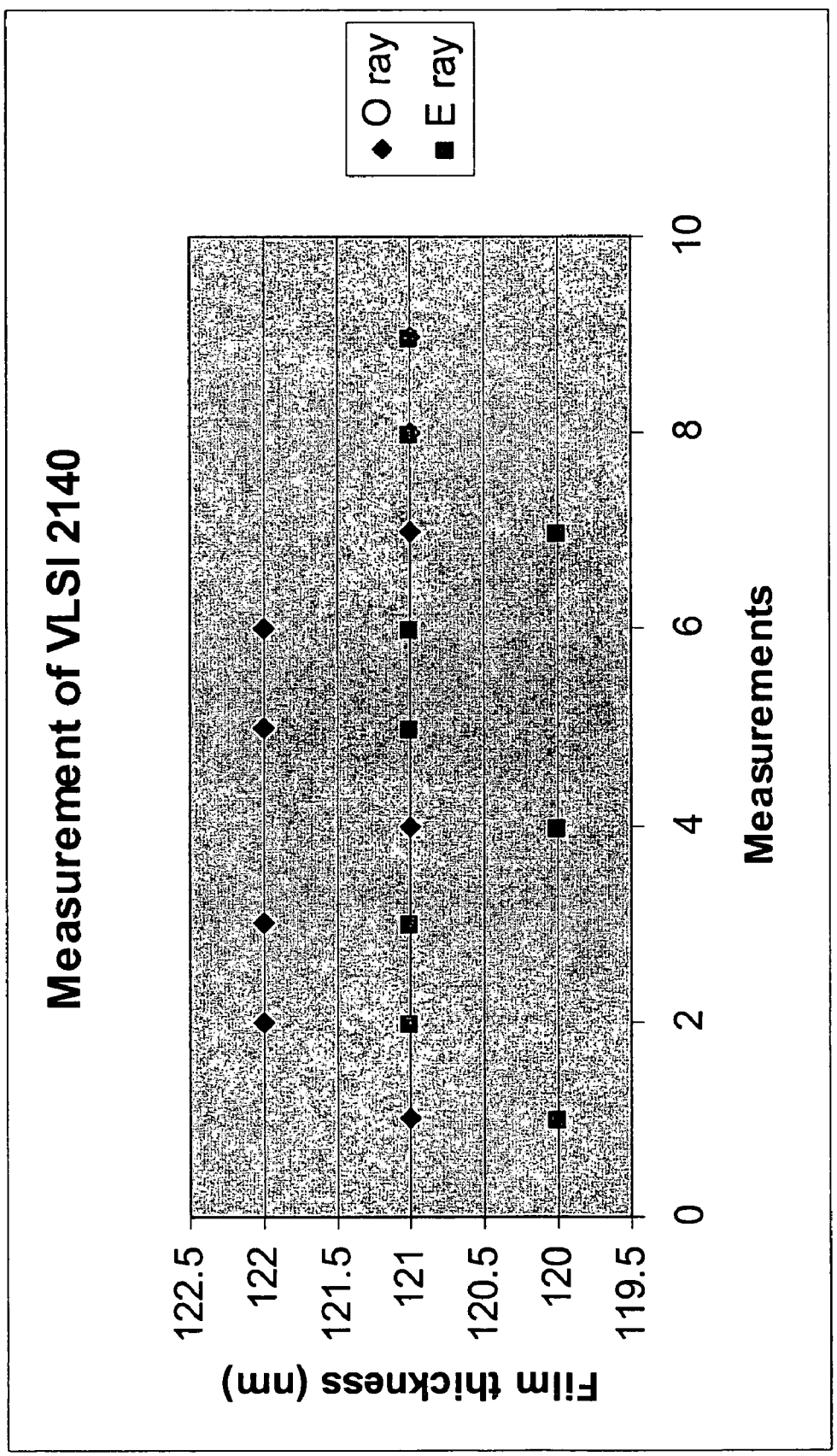
FIG. 6 shows the results of several measurements taken using different polarizations of incident light.

FIGS. 3-6 illustrate the method of the invention applied to the measurement of a $SiO_2$ film of approximately known thickness (121.5+/−3 nm) deposited over a Si substrate. FIG. 3 shows the correlogram 28 produced by the part under test. The spectral distribution 30 of the Fourier amplitude, F(k,d), derived from the correlogram 28 is shown in FIG. 4 as a function of wavenumber, together with the reference amplitude function 32 derived at the calibration step using a reference substrate of known reflectivity over the range of wavelengths of the light source. Although not necessary to practice the invention, a reference substrate with a substantially constant reflectivity, such as one coated with an aluminum film, may be used for convenience. It is noted that any material of known reflectivity that does not exhibit any absorption is suitable as a reference surface. FIG. 5 shows the plot of the error function 34 (labeled merit function) generated by comparing b(k,d), calculated from the Fourier amplitude 30, and b'(k,d), derived from Equation 4 using known values for $r_{01}$ and $r_{12}$. As explained above, the thickness corresponding to the minimum of the error function produces the desired film-thickness result.

Several measurements were taken using different polarizations of the incident light (labeled ordinary, O, and extra-ordinary, E) and the film thickness corresponding to each error-function minimum obtained as illustrated above is shown in FIG. 6. These results show that the average thickness of the film obtained with the Fourier-amplitude approach of the invention turned out to be 121.4 nm with a standard deviation of 0.53 nm, well within the thickness known a priori for the film.

Figure 7:
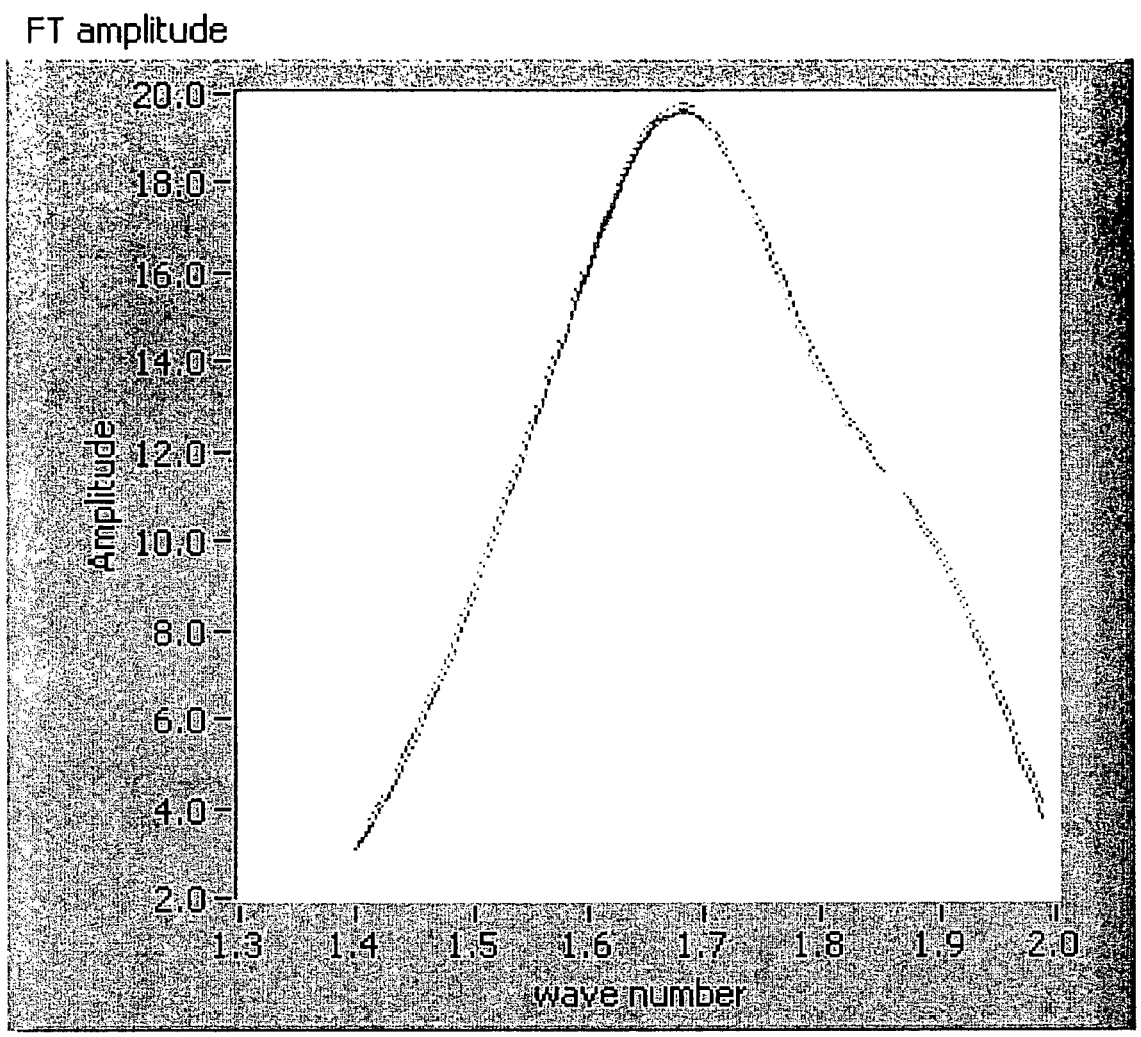
FIG. 7 shows the repeatability of the amplitude spectrum obtained in reflection from the same thin-film coating using five independent WLSI measurements.
Figure 8:
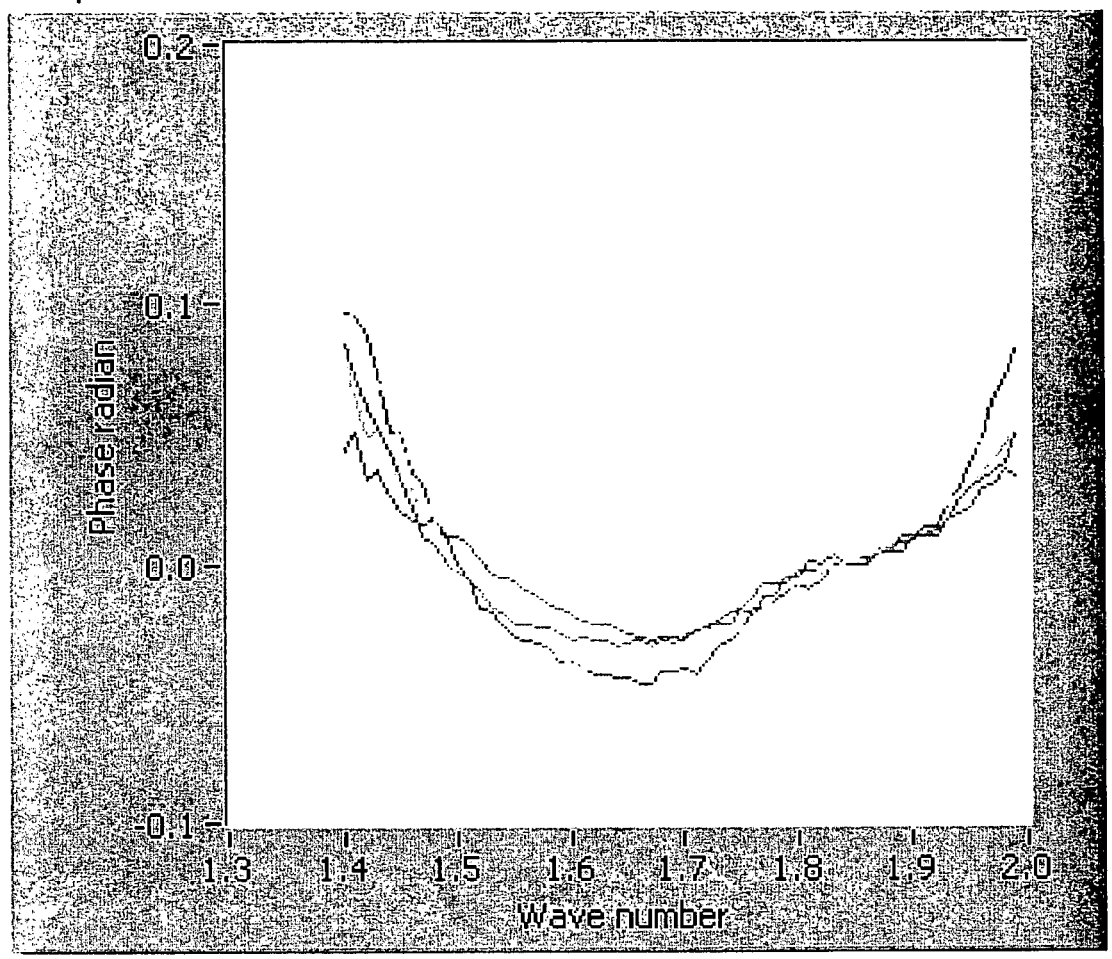
FIG. 8 shows the unreliability of the phase spectrum obtained in reflection from the same thin-film coating of FIG. 7 using five independent WLSI measurements.

The advantage of the Fourier-amplitude method of the invention over the prior-art Fourier-phase method was clearly demonstrated by observing the difference in the repeatability of results obtained by the two approaches. FIGS. 7 and 8 report a comparison of the amplitude and phase spectra obtained in reflection from the same thin-film coating (about 121.5 nm thick) using five independent WLSI measurements. FIG. 7 illustrates the fact that the amplitude spectral measurements proved to be very stable and therefore repeatable, while FIG. 8 shows that the phase spectral measurements varied considerably. As explained above, this is consistent with the smoothly varying nature of the signal amplitude, which leads to repeatable thickness measurements even for thin films with thickness below 100 nm.

The method of the invention may be implemented using any other type of interferometer, such as Mirau or Linnik. In such case, it is understood that the effect of the refractive angle θ would be significant and would have to be taken into account The invention may also be used, alternatively, to determine experimentally the refractive index of an isotropic thin film deposited on a known substrate when the thickness of the film is also known. This is based on the fact that the index of refraction of a medium varies with of the wavelength of the light propagating through it (that is, it depends on k). Accordingly, -the same sequence of experimental and data-manipulation steps is implemented, except that the theoretical Fourier amplitude b'(k,d) obtained from Equation 4 and used in the error function is treated as a function of the index of refraction by virtue of the phase-difference variable $\delta = 2knd\cos\theta$, that contains n which, in turn, depends on the wavenumber k.

As one skilled in the art would readily appreciate, the invention could be used also to determine concurrently both the thickness and the refractive index of an isotropic thin film coating a known substrate. The same sequence of experimental and data-manipulation steps would be implemented, but the theoretical Fourier amplitude b'(k) obtained from Equation 4 and used in the error function would be treated as a function of both thickness and index of refraction. Since minimization of such an error function would be likely to produce many local minima, some a-priori approximate knowledge about the thickness and index of refraction of the film would have to be used to converge to the minimum corresponding to the true values.

It is also noted that the thin-film thickness calculated according to the amplitude approach of the invention could be used in combination with the phase approach taught by Kim et al. (U.S. Pat. No. 6,545,763) to calculate the profile of the substrate. Because the thickness measurement of the present invention produces more precise information for very thin films, using the film thickness obtained from amplitude information in combination with the phase information produced by the Kim approach would yield overall better results.

The invention has been described in terms of Fourier transforms because they are advantageously used routinely in the art, but it is clear that the amplitude component of any linear transform comprises the same spectral information and should therefore by equally suitable to practice the invention. For instance, the frequency decomposition of a wavelet transform, a Hankel transform, or a Hilbert transform are expected to enable the invention using the same procedural approach. Accordingly, the term "linear transform" is used herein generically to refer to any transform that could be applied to a correlogram and advantageously decomposed to obtain spectral amplitude information suitable to practice this invention.

It is understood that the invention can be practiced in similar manner to measure the thickness of multiple layers stacked over a substrate. The only difference with respect to the procedure outlined above would be that different equations would be used to retrieve the amplitude required information (i.e., the amplitude and phase in Equation 1 would be functions of multiple films, while Equation 4 would be extended to a more general condition including multiple films). Otherwise, the method of the invention is equally applicable. It is also understood that the invention could be practiced without any calibration of the instrument so long as a correct optical model (empirical or theoretical) were known for the reference amplitude function S(k)a(k) (that is, the amplitude contribution of the source and reference beams and the detector response to the reflected beam as a function of wavelength).

In essence, the invention has demonstrated that the amplitude component of a linear transform of the spectrum of the correlogram produced by a thin-film/substrate combination can be used advantageously to determine the thickness of the thin film. The same technique can be applied with multiple thin films stacked over the substrate. Inasmuch as the measurement is based on information derived from the spectrum of the light used, as the thickness of the thin film decreases, the precision of the measurements is improved by a greater number of wavelengths present in the light source. Conversely, as the film thickness increases, a progressively narrower band is required to produce acceptable results. At the limit, even two wavelengths alone, if sufficiently separated to yield discernible data, would be sufficient to practice the invention.

The quality of the results obtained with this invention is obviously dependent on the accuracy of the vertical scan information used to extract the amplitude information. Therefore, every effort should be made to obtain good interferometric data. To that end, it is anticipated that a reference signal, such as taught in U.S. Pat. No. 6,624,894, or the zero crossing method commonly used in FTIR spectroscopy will be used in the process of acquisition of the intensity data utilized to produce the correlogram from which the linear transform is derived.

In view of the above, while the present invention has been shown and described herein in what is believed to be the most practical and preferred embodiments, it is recognized that departures can be made therefrom within the scope of the invention. For example, if the thin film consists of primarily absorptive material (such as a thin metal, a semiconductor or a color filter), the invention can be practiced in the same way so long as Equation 4 is modified to account for absorption. Similarly, the invention could be used to identify bi-refringent materials on the basis of the different results produced with light of different polarization. Therefore, the invention is not to be limited to the details disclosed herein but is to be accorded the full scope of the claims so as to embrace any and all equivalent processes and products.

I claim:

1. A method for determining a property of a thin film placed over a substrate, comprising the following steps:
   producing a test correlogram of said thin film over the substrate;
   generating a test linear transform of the test correlogram and extracting a test transform amplitude from the test linear transform;
   deriving a test-beam amplitude component of said test transform amplitude by removing a reference amplitude function, wherein the reference amplitude function comprises the product of the amplitude components contributed by the light source and the reference beam; and
   finding a value of said property of the thin film by comparing said test-beam amplitude component to a model test-beam amplitude function.

2. The method of claim 1, wherein said reference amplitude function is obtained by calibration using a reference substrate having a known reflectivity over a predetermined waveband.

3. The method of claim 2, wherein said calibration comprises the steps of:
   generating a calibration correlogram with a broadband light source included within said predetermined waveband;
   generating a calibration linear transform of the calibration correlogram;
   extracting a calibration transform amplitude from the calibration linear transform; and
   establishing said reference amplitude function from said calibration transform amplitude and said known reflectivity of the reference substrate, said reference amplitude function representing light-source and reference-beam amplitude components of the calibration transform amplitude.

4. The method of claim 3, wherein said known reflectivity of the reference substrate is substantially constant over said predetermined waveband.

5. The method of claim 3, wherein said reference amplitude function is established by dividing said calibration transform amplitude by a spectral amplitude of a test beam reflected from said reference substrate during said calibration steps.

6. The method of claim 1, wherein said test-beam amplitude component is calculated by dividing the test transform amplitude by said reference amplitude function.

7. The method of claim 1, wherein said finding step is carried out by defining an error function equal to a difference between said test-beam amplitude component and said model test-beam amplitude function, and by minimizing said error function with respect to said property of the thin film.

8. The method of claim 1, wherein said model test-beam amplitude function is derived from a theoretical expression modeling a reflection from said thin film over the substrate.

9. The method of claim 8, wherein said theoretical expression is $$\rho(k, d) = \frac{r_{01} + r_{12}\exp(-i2\delta)}{1 + r_{01}r_{12}\exp(-i2\delta)}$$
$$= b'(k, d)\exp[i\phi(k, d, \theta)],$$

where $\rho(k,d)$ is a coefficient of total reflection, $r_{01}$ is a Fresnel coefficient of reflection at an incident-medium to film boundary, $r_{12}$ is a Fresnel coefficient of reflection at a film to substrate boundary, $\delta = 2$ knd $\cos \theta$ is a phase difference between consecutive reflections off the film, n is an index of refraction of the film at wavenumber k, $\theta$ is a refractive angle in the film, d is a film thickness, and $b'(k,d)$ is said theoretical test-beam amplitude function.

10. The method of claim 1, wherein said reference amplitude function is derived from an optical model.

11. The method of claim 1, wherein said linear transform is a Fourier transform.

12. The method of claim 3, wherein said linear transform is a Fourier transform.

13. The method of claim 1, wherein said property is a thickness of the thin film.

14. The method of claim 3, wherein said property is a thickness of the thin film.

15. The method of claim 1, wherein said property is an index of refraction of the thin film.

16. The method of claim 3, wherein said property is an index of refraction of the thin film.

17. The method of claim 3, wherein said linear transform is a Fourier transform; said property is a thickness of the thin film; said reference amplitude function is established by dividing said calibration transform amplitude by a spectral amplitude of a test beam reflected from said reference substrate during the calibration steps; said test-beam amplitude component is calculated by dividing the test transform amplitude by said reference amplitude function; said finding step is carried out by defining an error function equal to a difference between said test-beam amplitude component and said theoretical test-beam amplitude function, and by minimizing said error function with respect to said thickness of the thin film; and said model test-beam amplitude function is derived from a theoretical expression modeling a reflection from said thin film over the substrate.

18. The method of claim 3, wherein said linear transform is a Fourier transform; said property is an index of refraction of the thin film; said reference amplitude function is established by dividing said calibration transform amplitude by a spectral amplitude of a test beam reflected from said reference substrate during the calibration steps; said test-beam amplitude component is calculated by dividing the test transform amplitude by said reference amplitude function; said finding step is carried out by defining an error function equal to a difference between said test-beam amplitude component and said theoretical test-beam amplitude function, and by minimizing said error function with respect to said index of refraction of the thin film; and said model test-beam amplitude function is derived from a theoretical expression modeling a reflection from said thin film over the substrate.

19. The method of claim 13, further including the step of determining a profile of said substrate using said thickness of the thin film.

20. The method of claim 19, wherein said step of determining a profile of the substrate includes utilizing phase information extracted from said test correlogram.

21. The method of claim 1, wherein said thin film includes multiple layers, said property is a thickness of each layer, and said thickness of each layer is determined using a corresponding model test-beam amplitude function.

22. The method of claim 1, wherein said steps are repeated using light of different polarization to identify a bi-refringent thin film.

* * * * *